United States Patent [19]

Brown

[11] Patent Number: 5,628,309

[45] Date of Patent: May 13, 1997

[54] METER FOR ELECTRICALLY MEASURING AND RECORDING INJECTION SYRINGE DOSES

[75] Inventor: Stephen J. Brown, Mountain View, Calif.

[73] Assignee: Raya Systems, Inc., Mountain View, Calif.

[21] Appl. No.: 591,308

[22] Filed: Jan. 25, 1996

[51] Int. Cl.$^6$ .................................................. A61B 5/00
[52] U.S. Cl. ....................... 128/632; 604/65; 128/DIG. 1
[58] Field of Search ..................................... 128/632, 637, 128/DIG. 1; 604/65, 68, 207, 211, 218, 224, 245, 66, 67; 73/290 R, 291; 141/18, 311 R

[56] References Cited

U.S. PATENT DOCUMENTS 5,368,562 11/1994 Blomquist et al. ........................ 604/65
5,536,249 7/1996 Castellano et al. ........................ 604/65

*Primary Examiner*—Angela D. Sykes
*Assistant Examiner*—Bryan K. Yarnell
*Attorney, Agent, or Firm*—Lumen Intellectual Property Services

[57] ABSTRACT

A method and device for electrically measuring and recording injection syringe doses. The device has a voltage generator for applying a voltage to an input terminal of a syringe. The device also has a measuring instrument for measuring an electrical response from the syringe. The electrical response results from the voltage and indicates the size of the dose in the syringe. An electronic memory records the measurement of the electrical response so that there is an electronic record of the dose injected. A data port is connected to the electronic memory so that the dose records may be transmitted to a host computer.

17 Claims, 7 Drawing Sheets

5,628,309

METER FOR ELECTRICALLY MEASURING AND RECORDING INJECTION SYRINGE DOSES

BACKGROUND

1. Field of the Invention

The present invention relates to the field of measuring devices for self-administration of a medicine, and in particular to a meter for electrically measuring and recording injection syringe doses.

2. Description of Prior Art

Electronic medical records have a significant advantage over paper medical records. With electronic medical records, health care providers and patients can better store, retrieve, and share medical information. Electronic medical records are particularly advantageous for the treatment of chronically ill patients who must self-monitor and self-inject medications on a daily basis. In therapies such as self-administration of insulin, human growth hormone, or other medications, patients themselves perform the injections and keep records.

Unfortunately, no adequate system exists for these patients to electronically record information about the doses they inject. That is because these injections are most commonly delivered with disposable syringes that have no mechanism for electronically recording the dose information. The patient is burdened with the task of injecting a dose and then manually recording the dose amount into a log.

Because of the frequency of such injections, often several times a day for diabetics, it becomes difficult to keep accurate records. Indeed, studies have shown that a patient's own records and recollections are often incomplete and inaccurate. Additionally, a patient may intentionally cheat while making self-recorded entries in an attempt to create a log that will please their doctor. In the long-term this makes patient monitoring extremely difficult and jeopardizes the therapy, possibly even endangering the patient's life.

Attempts have been made at developing electronic management systems for assisting patients in self-administered drug programs. For example, U.S. Pat. No. 5,019,974 issued to Andreas Beckers describes a hand-held recorder that can interface with a master computer. The recorder has a programmed computer, into which patient therapy information is entered via a keyboard, and a display for displaying treatment therapy guidelines to the patient. The recorder also includes a blood glucose meter connected to the programmed computer to help develop the therapy guidelines.

U.S. Pat. No. 5,307,263 issued to applicant on Apr. 26, 1994 describes a small, hand-held, microprocessor-based unit for self-care health monitoring. The unit has a program cartridge for controlling the operation of the unit, as well as switches for the patient to enter dose information. The unit also includes a blood glucose meter for monitoring the patient's condition.

Unfortunately, none of these inventions allows automatic electrical recording of the amount of medication injected. After injecting a dose, the patient must manually enter the dose information into a microprocessor-based system, using switches or keys. Although this is an improvement over keeping written records on paper, the effectiveness of the drug program is still limited by the patient's recollections and recordings, which are unreliable. Thus, there is a need for a device that provides an objective and accurate electronic record of injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

While this apparatus comes closest to solving the problem, it involves many complicated steps of weighing syringes, scanning in bar codes, etc. These complex procedures as well as the high cost of the apparatus preclude effective home use. Additionally, the apparatus cannot be easily carried by the patient for measuring and recording doses while away from home. Thus, no cost-effective dosage meter exists that can electrically measure and record dose information from a syringe. Further, no electrical dosage meter exists that is easy to use and portable.

OBJECTS AND ADVANTAGES OF THE INVENTION

In view of the above, it is an object of the present invention to provide a dosage meter that can electrically measure and record dose information from an injection syringe. It is another object of the invention to provide an electrical dosage meter that is hand-held, easy to use, and cost-effective. A further object of the invention is to provide an electrical dosage meter that incorporates a blood glucose meter for aiding a patient in a self-administered medication program.

These and other objects and advantages will become more apparent after consideration of the ensuing description and the accompanying drawings.

SUMMARY OF THE INVENTION

The invention presents a method and device for electrically measuring and recording a dose contained in an injection syringe. The device has a voltage generator for applying a voltage to an input terminal of the syringe. The device also includes a measuring instrument for measuring an electrical response from the syringe. The electrical response results from the applied voltage and indicates the size of the dose contained in the syringe.

In one embodiment, the electrical response is an electric current flowing between the input terminal and an output terminal of the syringe. The amount of the electric current indicates the size of the dose contained in the syringe. The measuring instrument is an ammeter electrically connected to the output terminal of the syringe. The ammeter measures the amount of electric current at the output terminal.

In a second embodiment, the electrical response is an electric current flowing from the input terminal to one of a number of output terminals of the syringe. The size of the dose contained in the syringe determines which one output terminal has the electric current. The measuring instrument is a circuit reader electrically connected to the output terminals. The circuit reader reads each output terminal to determine which one has the electric current.

In a third embodiment, the electrical response is a voltage magnetically induced in a conducting loop of the device. The amount of induced voltage indicates the size of the dose contained in the syringe. The measuring instrument is a voltage meter connected to the conducting loop. The voltage meter measures the amount of magnetically induced voltage in the conducting loop.

In a fourth embodiment, the electrical response is a capacitance between a conducting plate and a conducting ring of the syringe. The amount of capacitance between the conducting plate and conducting ring indicates the size of the dose contained in the syringe. The measuring instrument is a capacitance meter set up to measure the capacitance between the conducting plate and conducting ring.

The measuring instrument is connected to an electronic memory, which records the measurement of the electrical response. A data port is connected to the electronic memory so that the electronic dose records may be transmitted through the data port to a host computer. In a particularly advantageous embodiment, the device also includes a testing instrument connected to the electronic memory for testing a physical condition of a patient, producing a digital value representative of the physical condition, and recording the digital value in the electronic memory. Also in this embodiment, the device has a display for displaying the digital value representative of the physical condition and the electronic dose records.

DESCRIPTION

Figure 1:
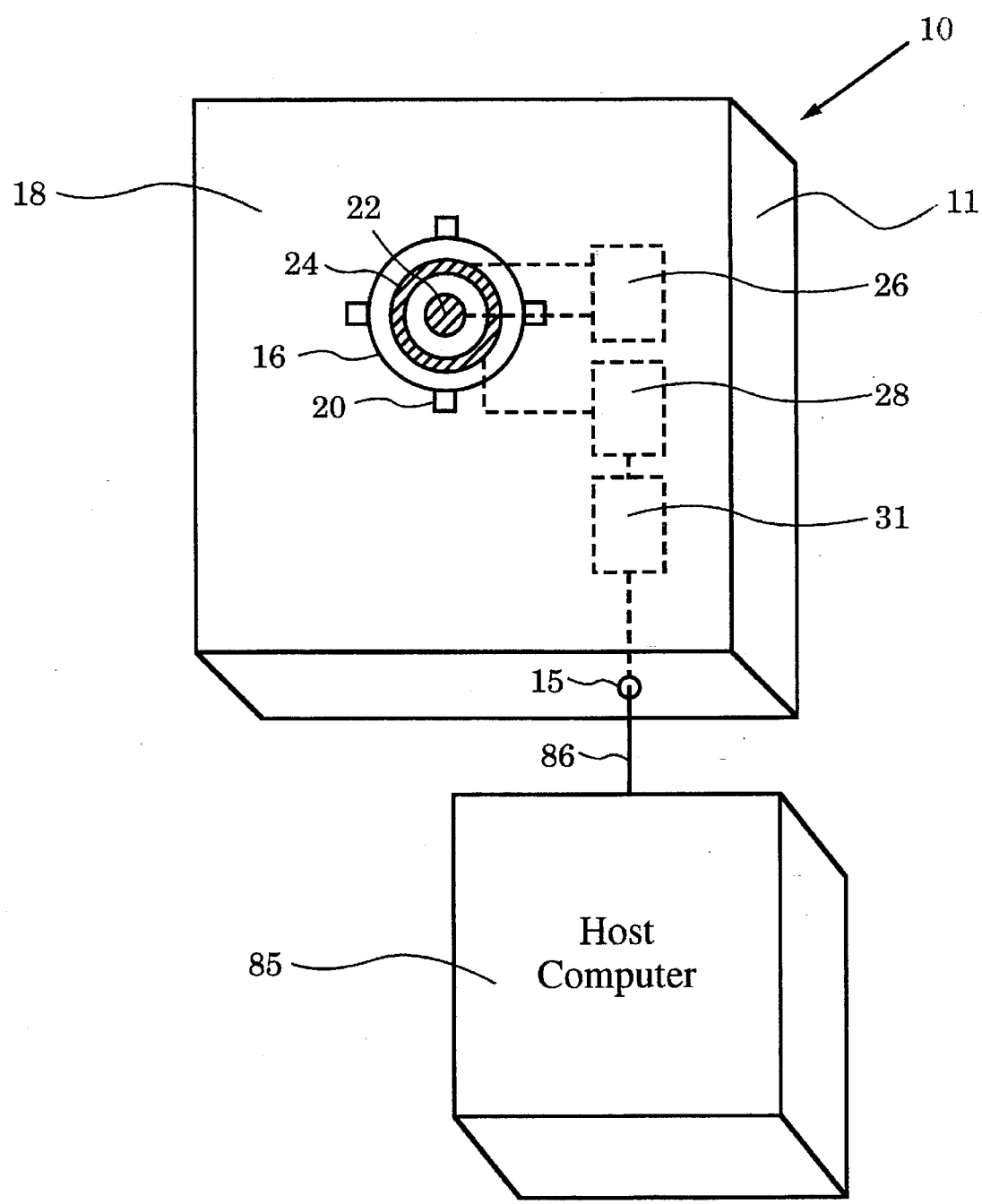
FIG. 1 is a schematic view of a metering device according to the invention and a host computer.
Figure 2:
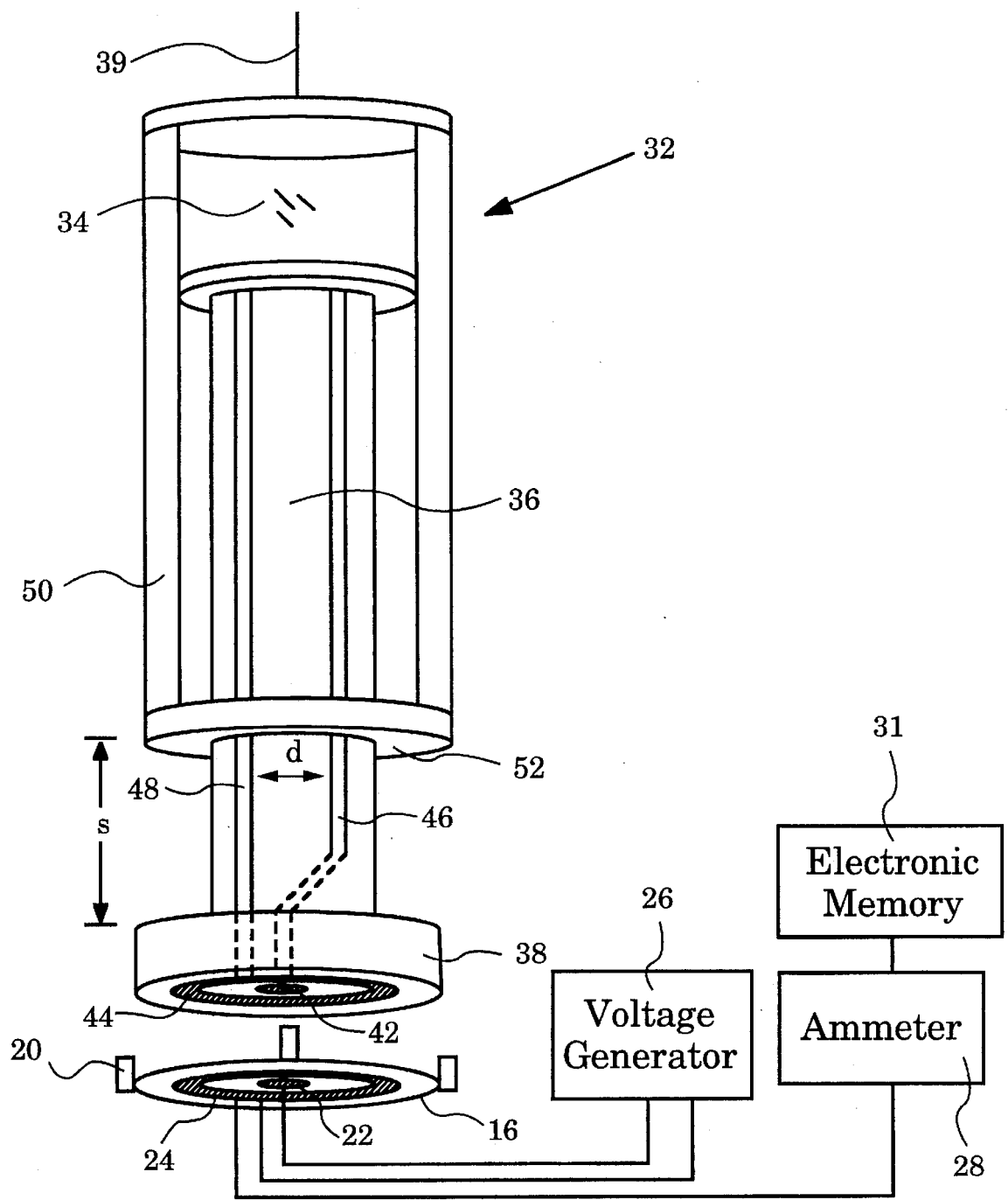
FIG. 2 is a schematic view and partial block diagram of an injection syringe being placed on the metering device of FIG. 1 for dose measurement.

The preferred embodiment of the invention is illustrated in FIG. 1 and FIG. 2. Referring to FIG. 1, a metering device 10 has a housing 11 for holding the components of device 10. Housing 11 is sufficiently compact to allow device 10 to be hand-held and carried by a patient. The top surface of housing 11 has a face plate 18. A circular placement field 16 is delineated on face plate 18. Placement field 16 is bordered on four sides by rigid positioning studs 20.

Located concentrically inside placement field 16 are a circular input contact 22 and a ring-shaped output contact 24. Both input contact 22 and output contact 24 are made of an electrically conductive material, preferably copper. Below face plate 18, contacts 22 and 24 are connected to a voltage generator 26 as indicated. Voltage generator 26 is of the type that applies a constant voltage difference V across input contact 22 and output contact 24. The constant voltage V generated by generator 26 can be in the range of 1 to 20 volts, with a preferred value of 9 volts so that a conventional 9 volt battery can be used as generator 26.

FIG. 2 illustrates in detail the positioning of a cap 38 of a syringe 32 on placement field 16 for dose measurement.

Cap 38 is a circular disk having an outer surface of the same shape and dimensions as placement field 16, such that positioning studs 20 fit exactly around the perimeter of the outer surface of cap 38 when cap 38 is pressed against placement field 16. Located concentrically on the outer surface of cap 38 are a circular input terminal 42 and a ring-shaped output terminal 44. Both input terminal 42 and output terminal 44 are made of an electrically conductive material, preferably copper. Terminal 42 has the same shape and dimensions as contact 22 and terminal 44 has the same shape and dimensions as contact 24. Terminals 42 and 44 are located on cap 38 such that they establish electrical contact with input contact 22 and output contact 24 respectively when cap 38 is pressed against placement field 16.

Inside syringe 32, input terminal 42 and output terminal 44 are connected to a conducting strip 46 and a resistive strip 48 respectively. Resistive strip 48 is made of a material whose resistance per unit length is several orders of magnitude larger than the resistance per unit length of conducting strip 46. In the preferred embodiment, the resistance per unit length of conducting strip 46 is 1 Ohm/m and the resistance per unit length of resistive strip 48 is 1,000 Ohm/m. Strip 46 is routed inside cap 38 and a short portion, typically about 5 to 10 mm, of strip 46 is molded into a plunger 36. Then strip 46 emerges on the surface of plunger 36. Similarly, resistive strip 48 is also routed through cap 38 and then emerges on the surface of plunger 36 parallel with strip 46 at a distance d away. Distance d is chosen to ensure that no current can bridge over from strip 46 to strip 48.

Plunger 36 is inserted in one end of a hollow barrel 50. The other end of barrel 50 has a needle 39 for injecting a dose 34 contained in barrel 50. Dose 34 occupies the inner volume of barrel 50 between plunger 36 and the end of barrel 50 having needle 39. The end of barrel 50 through which plunger 36 is inserted has a conducting rim 52. Rim 52 contacts plunger 36 as well as strips 46 and 48 at the location where plunger 36 enters barrel 50.

Rim 52 is lined with an electrically conductive material, preferably copper. Some of the electrically conductive material wraps inside barrel 50 to ensure a good electrical contact with strips 46 and 48. This creates a conducting path (42, 46, 52, 48, 44) from terminal 42 to terminal 44. The length of this conducting path depends on the distance s between cap 38 and rim 52. Its total length approximately equals to 2s+d. In other words, the length of the conducting path decreases the further plunger 36 advances inside barrel 50.

Referring again to FIG. 1, an ammeter 28 is connected to output contact 24 such that ammeter 28 can measure an electric current I flowing through the conducting path between contacts 22 and 24. In the preferred embodiment, ammeter 28 is of the type that produces a digital measurement of current I. In an alternative embodiment, ammeter 28 is of the type that produces an analog measurement of current I. In this alternative embodiment, ammeter 28 is connected to an analog to digital converter (not shown) that converts the analog measurement of current I into a digital measurement.

An electronic memory 31 is connected to ammeter 28 such that memory 31 can record the digital measurement of current I produced by ammeter 28. A data port 15 is located on the outer surface of housing 11. Data port 15 is connected to memory 31 such that the digital measurement of current I recorded in memory 31 can be transmitted through data port 15 to a host computer 85 through a data connection cord 86.

The operation of the preferred embodiment is shown in FIG. 2. Before injecting dose 34, the patient first presses the outer surface of cap 38 against placement field 16. When cap 38 is properly pressed between positioning studs 20, input contact 22 and output contact 24 establish electrical contact with input terminal 42 and output terminal 44 respectively. Meanwhile, voltage generator 26 applies voltage difference V across input contact 22 and output contact 24. Voltage V causes electric current I to flow through the conducting path comprising input terminal 42, conducting strip 46, rim 52, resistive strip 48, and output terminal 44.

Based on Ohm's law, which states that I=V/R, current I is inversely proportional to the total resistance R of the conducting path. Because voltage V is constant, current I varies only with total resistance R. This total resistance R depends on the length of the conducting path, which was shown to equal approximately 2s+d. Of this distance s is the length of resistive strip 48 between cap 38 and rim 52. Since the resistance of conducting strip 46 and rim 52 are very small in comparison to the resistance of strip 48, an approximation is made. The total resistance R of the conducting path is taken to be the resistance constituted by length s of resistive strip 48, the resistance of the other parts of the path being negligible.

Consequently, a measurement of current I, which depends on total resistance R, produces electrical data indicating how far plunger 36 is inserted inside barrel 50. Because dose 34 occupies the inner volume of barrel 50 between plunger 36 and the end of barrel 50 having needle 39, the position of plunger 36 inside barrel 50 defines the size of dose 34. Thus, a measurement of current I indicates the size of dose. 34 contained in barrel 50. The measurement of current I is performed by ammeter 28 and electronically recorded in memory 31. The measurement of current I recorded in memory 31 is later transmitted through data port 15 to host computer 85, as shown in FIG. 1. Host computer 85 converts the measurement of current I into the corresponding size of dose 34, using one of the conversion techniques discussed in the second embodiment below.

The advantage of the device described in this preferred embodiment is that it can electrically measure doses of a medication directly from an injection syringe and digitally record these measurements. The patient is not burdened with manually entering the dose information into a log. Additionally, the dose information recorded is more accurate than a patient's manual records, which have been shown to be unreliable.

Figure 3:
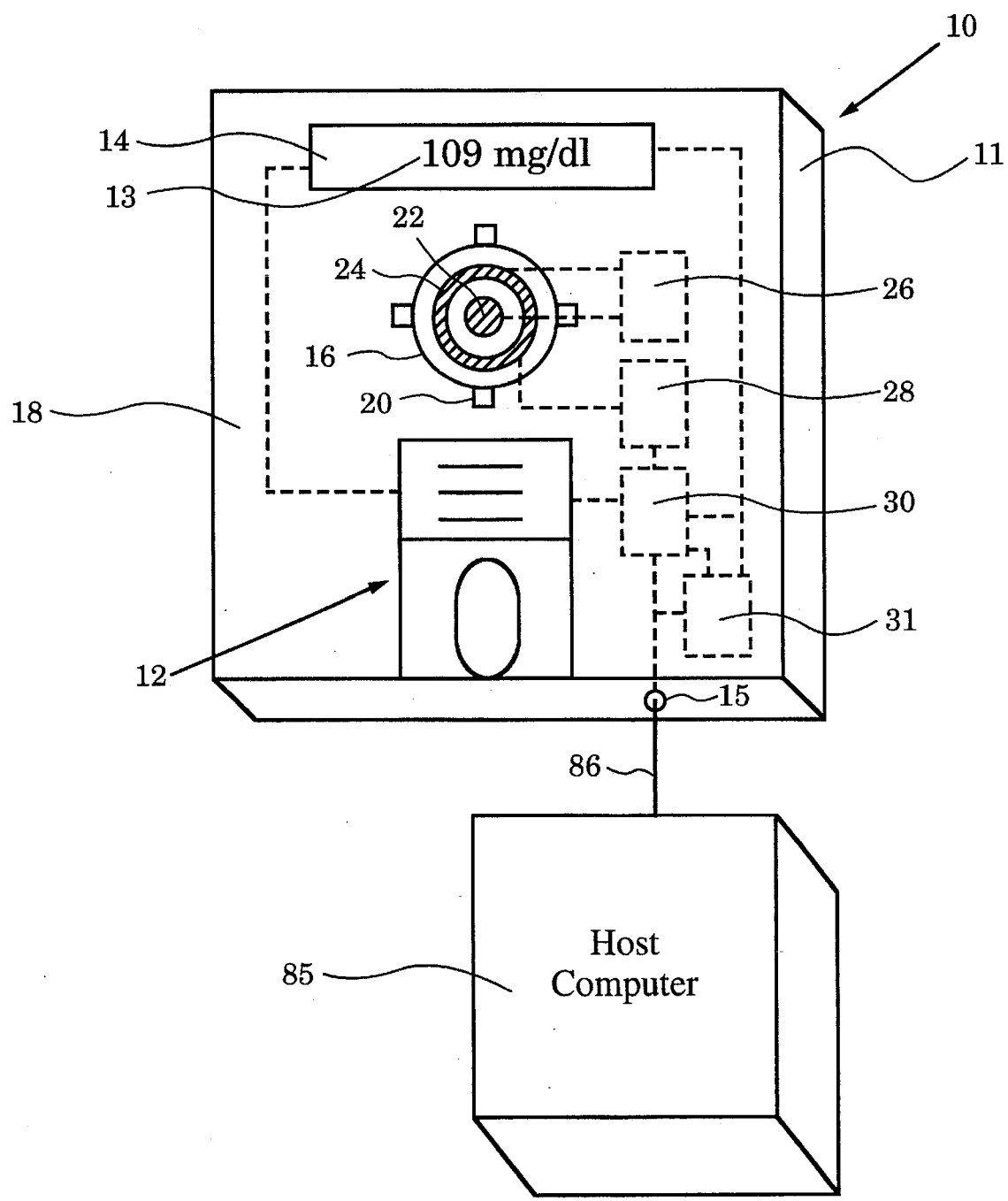
FIG. 3 is a schematic view of another metering device according to the invention and a host computer.

A second embodiment of the invention is shown in FIG. 3. In this second embodiment, a microprocessor 30 is connected between ammeter 28 and electronic memory 31 such that microprocessor 30 can receive the digital measurement of current I from ammeter 28 and record digital output in memory 31. Microprocessor 30 is programmed to convert the measurement of current I into a digital value representative of the size of dose 34, as will be explained in the operation section below.

In this embodiment, microprocessor 30 is preprogrammed during the manufacturing of device 10 with the values necessary to make this conversion. The necessary values are the amount of voltage V applied by generator 26, the length and inner volume capacity of barrel 50, the length of plunger 36, and the resistance per unit length of strip 48. Of course, other methods of programming microprocessor 30 with the dimensions of syringe 32 are also possible. In one alternative embodiment, device 10 has a user-controllable interface (not shown) to microprocessor 30 so that the user programs microprocessor 30 with the dimensions of syringe 32 before measuring and recording dose 34.

In the second embodiment, device 10 also has a meter 12 for testing a physical condition of a patient. Meter 12 is of the type that can collect bodily fluid from a patient, test the bodily fluid, and produce a digital value 13 representative of the physical condition of the patient. Meter 12 is connected to memory 31 such that memory 31 records value 13. In this embodiment, meter 12 is a blood glucose meter that collects blood from a patient's finger. The value 13 produced by the blood glucose meter is the patient's blood glucose level. A display 14 is connected to meter 12 and microprocessor 30 such that display 14 can display blood glucose and dose information for a patient to read.

There are two differences in the operation of the second embodiment from the operation of the preferred embodiment described above. First, before selecting a dose, the patient places his finger on meter 12. Meter 12 draws blood from the patient's finger, tests the blood, and produces digital value 13 representative of the patient's blood glucose level. Meter 12 sends this information to memory 31, which records value 13. Value 13 is later transmitted through data port 15 to host computer 85 along with the dose record. Meter 12 also sends value 13 to display 14, and display 14 displays value 13 as a "blood glucose level" measurement. The patient can now use this measurement to determine a size of dose 34 to inject.

The second difference from the preferred embodiment is that the digital measurement of current I is not recorded into memory 31. Instead, microprocessor 30 converts the digital measurement of current I into a corresponding digital value representative of the size of dose 34, and this corresponding digital value is recorded in memory 31. To make this conversion, microprocessor 30 receives the digital measurement of current I from ammeter 28. Microprocessor 30 then calculates the total resistance R of the conducting path by dividing known voltage V by current I. The total resistance R is then divided by the known resistance per unit length of strip 48 to calculate distance s. Distance s is subtracted from the total length of plunger 36 to calculate the length of plunger 36 inside barrel 50.

By subtracting the length of plunger 36 inside barrel 50 from the total length of barrel 50 and then dividing the result by the total length of barrel 50, microprocessor 30 calculates the percentage of the inner volume capacity of barrel 50 containing dose 34. By multiplying this percentage by the known inner volume capacity of barrel 50, microprocessor 30 calculates the size of dose 34 contained in syringe 32.

Of course, other methods of converting the measurement of current I into a digital value representative of the size of dose 34 are possible in alternative embodiments. In one alternative embodiment, microprocessor 30 is pre-programmed with a table of possible values of current I, and a corresponding dose size for each possible value. Upon receiving the measurement of current I, microprocessor 30 looks up the corresponding dose size in the table.

Once microprocessor 30 has produced the digital value representative of the size of dose 34, it passes the value to memory 31 and display 14. Memory 31 records the digital value and display 14 displays it as a "dose selected" measurement. This alerts the patient that the injection of dose 34 can now be performed. After injecting dose 34, the patient transmits the dose record recorded in memory 31 through data port 15 to host computer 85.

The advantage of this second embodiment is that device 10 records digital values representative of both the patient's blood glucose level and the size of dose 34. Additionally, current I is converted to a digital value representative of the size of dose 34 before being recorded in memory 31 and transmitted to host computer 85. This eliminates the need for host computer 85 to make the conversion. Other than the two differences mentioned, the operation and advantages of this second embodiment are identical to the operation and advantages of the preferred embodiment described above.

Figure 4:
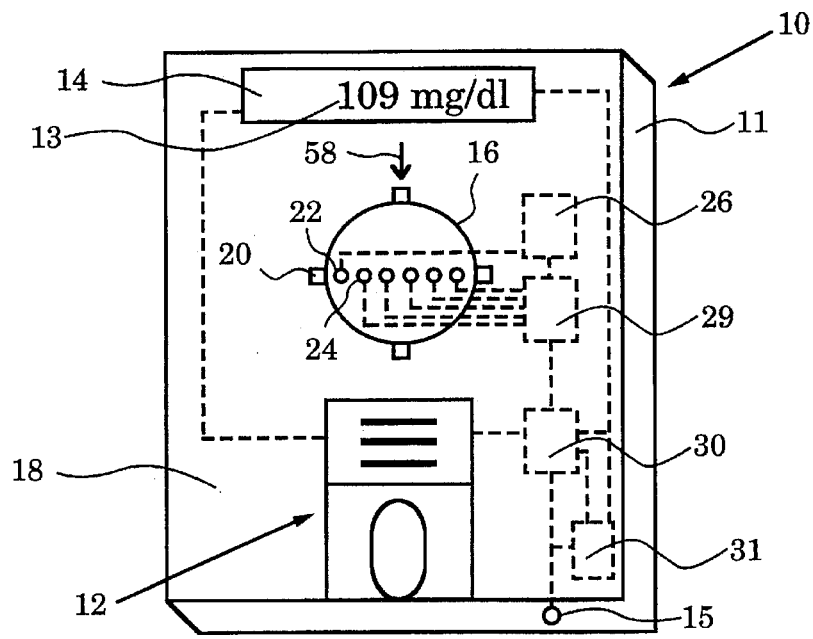
FIG. 4 is a schematic view of another metering device according to the invention.
Figure 5:
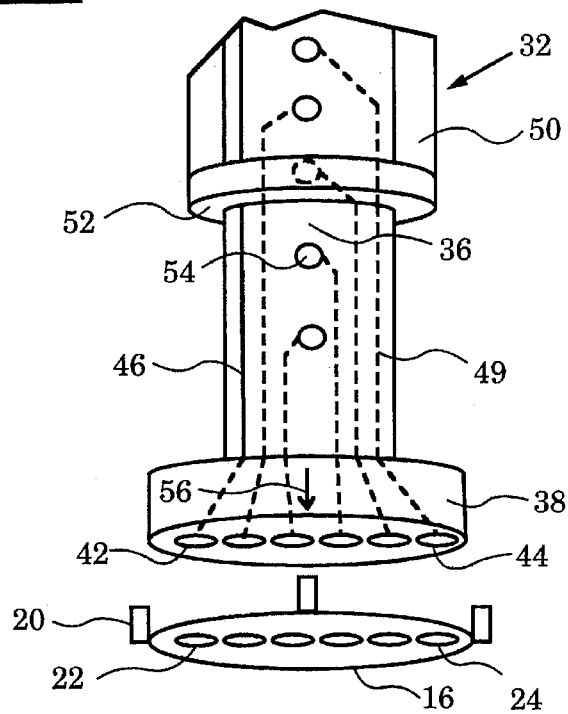
FIG. 5 is a schematic view of another injection syringe being placed on the metering device of FIG. 4 for dose measurement.

A third embodiment of the invention is shown in FIG. 4 and FIG. 5. Throughout the description of the third embodiment, references will be made to five output contacts 24, five output terminals 44, five contact points 54, and five output strips 49. The number five is used for illustrative purposes only. Any number in the range from 1 to 20 would also be possible. Referring to FIG. 4, metering device 10 differs from the preferred embodiment in that it now includes five output contacts 24 and one input contact 22 located within placement field 16. Input contact 22 and five output contacts 24 are connected to voltage generator 26 below face plate 18. Voltage generator 26 is connected to apply a voltage difference V across input contact 22 and all five output contacts 24.

A circuit reader 29 is electrically connected to output contacts 24 such that it can determine which one of contacts 24 has an electric current I, as will be described in the measuring process below. Electronic memory 31 is connected to circuit reader 29 so that it can record the readings of circuit reader 29 regarding which one of output contacts 24 has electric current I. Additionally, face plate 18 now has a positioning arrow 58 for indicating the proper orientation of cap 38 on placement field 16.

FIG. 5 illustrates in detail the positioning of cap 38 of syringe 32 on placement field 16 for dose measurement. Like the preferred embodiment described above, the end of barrel 50 through which plunger 36 is inserted has conducting rim 52. Rim 52 is lined with an electrically conductive material, preferably copper. Some of the conductive material wraps inside barrel 50 such that rim 52 contacts an outer surface of plunger 36. The outer surface of plunger 36 contacting rim 52 has five electrical contact points 54. Contact points 54 are made of an electrically conductive material, preferably copper.

The distance measured along the axis of plunger 36 from the edge of any contact point 54 to the edge of an adjacent contact point 54 is greater than the width of rim 52. This ensures that for any position of plunger 36 inside barrel 50, no more than one contact point 54 may contact rim 52 at the same time. Contact points 54 are arranged on the surface of plunger 36 such that the position of plunger 36 inside barrel 50 determines which one contact point 54 contacts rim 52. As was explained in the preferred embodiment above, the position of plunger 36 inside barrel 50 also defines the size of dose 34 contained in barrel 50. Thus, a determination of which one contact point 54 is contacting rim 52 also determines the size of dose 34 contained in barrel 50.

Five output terminals 44 are electrically connected to five contact points 54 by five output strips 49. Each contact point 54 is electrically connected to a different one output terminal 44. Output strips 49 are made of an electrically conductive material, preferably copper wire. They connect output terminals 44 to contact points 54 without contacting rim 52. In one embodiment, output strips 49 are routed from output terminals 44 through cap 38 and inside plunger 36 before connecting to contact points 54. In an alternative embodiment, output strips 49 are routed from output terminals 44 through cap 38 and molded into the surface of plunger 36 before connecting to contact points 54. Input terminal 42 is electrically connected to rim 52 by strip 46.

Strip 46 is connected at one end to input terminal 42, and then routed through cap 38 and along the outer surface of plunger 36, such that strip 46 contacts rim 52 whenever any one of contact points 54 contacts rim 52.

Input contact 22 and five output contacts 24 are located within placement field 16 such that when cap 38 is pressed against placement field 16 in a correct orientation, input terminal 42 establishes electrical contact with input contact 22 and each of five output terminals 44 contacts a different one of five output contacts 24. Cap 38 has a positioning arrow 56 located on its side surface such that when cap 38 is placed on placement field 16 With positioning arrow 56 aligned with positioning arrow 58, the correct orientation of cap 38 on placement field 16 is achieved.

The operation of the third embodiment is shown in FIG. 4 and FIG. 5. Before injecting dose 34, the patient positions plunger 36 in barrel 50 so that one contact point 54 is contacting rim 52. The patient then presses cap 38 of syringe 32 against placement field 16. When cap 38 is pressed between positioning studs 20 with arrow 56 aligned with arrow 58, input terminal 42 establishes electrical contact with input contact 22 and each of five output terminals 44 establishes electrical contact with a different one of five output contacts 24.

Voltage generator 26 applies voltage difference V across input contact 22 and output contacts 24. Voltage difference V causes electric current I to flow through a circuit comprising input contact 22, input terminal 42, strip 46, rim 52, the one contact point 54 contacting rim 52, the one output terminal 44 electrically connected to that one contact point 54, and the one output contact 24 contacting that one output terminal 44. Because each output contact 24 has electric current I only when plunger 36 has a defined position in barrel 50, a reading of the output contacts 24 produces electrical data indicating the position of plunger 36 inside barrel 50. The position of plunger 36 inside barrel 50 also indicates the size of dose 34 contained in barrel 50. Thus, the size of dose 34 can be determined by knowing which output contact 24 has electric current I.

Circuit reader 29 reads each output contact 24 to determine the one output contact 24 that has electric current I. Circuit reader 29 passes the output contact information to memory 31, which records it. Once the output contact information indicating the size of dose 34 has been recorded in memory 31, the operation and advantages of this embodiment are the same as the operation and advantages of the preferred embodiment described above.

Figure 6:
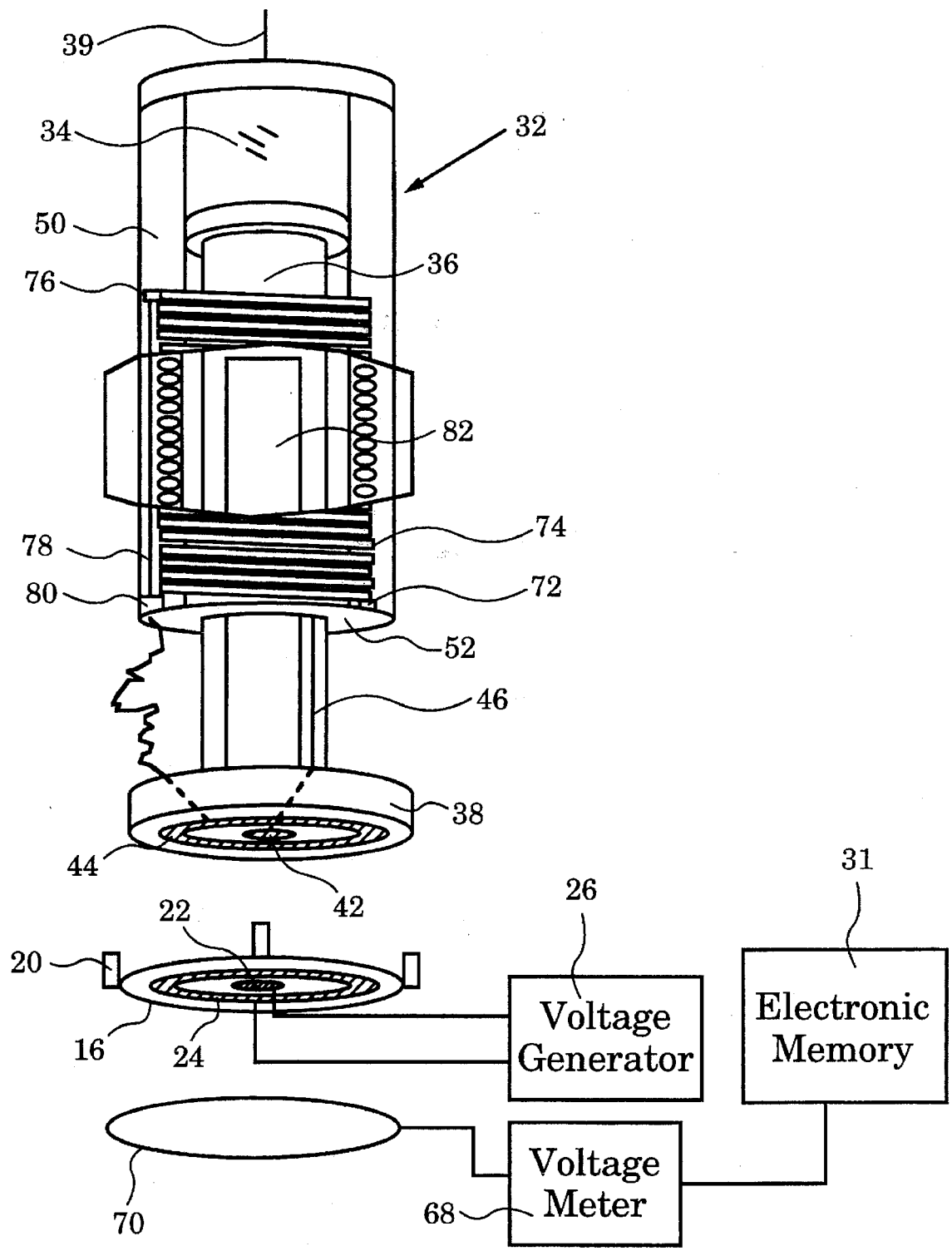
FIG. 6 is a schematic view, partial cross sectional view, and partial block diagram of another injection syringe being placed on another metering device for dose measurement.

A fourth embodiment of the invention, designed to measure magnetically induced voltages from syringe 32, is illustrated in FIG. 6. Device 10 now has a conducting loop 70 located below placement field 16. Loop 70 is made of an electrically conductive material In this embodiment, the diameter of loop 70 is equal to the diameter of field 16. In alternative embodiments, loop 70 is larger than field 16. A voltage meter 68 is connected to loop 70. Voltage meter 68 is of the type that can measure magnetically induced voltages in loop 70.

Referring to syringe 32, rim 52 is connected to a first terminal 72 of an inductor 74. Inductor 74 extends inside the wall of barrel 50 along two thirds of the length of barrel 50. At its other end, inductor 74 has a second terminal 76 One end of a connecting line 78 is connected to second terminal 76 of inductor 74. The other end of connecting line 78 is routed through the wall of barrel 50, the space between barrel 50 and plunger 36, and through cap 38 to output terminal 44. At rim 52, line 78 is insulated with an insulation sleeve 80 to prevent electrical contact with the conductive material lining rim 52.

A magnetically active core 82 is embedded concentrically inside plunger 36. Core 82 is cylindrical and has a length equal to two thirds of the length of barrel 50. Core 82 is positioned in plunger 36 so that the ends of core 82 are exactly aligned with the ends of inductor 74 when plunger 36 is fully inserted into barrel 50. Core 82 is made of a diamagnetic or paramagnetic material, or contains such material in its bulk, such that core 82 acts as magnetically responsive element within inductor 74. In this embodiment, core 82 is made of shavings of a diamagnetic metal embedded inside an inert material, e.g. plastic.

The operation of the fourth embodiment differs from the operation of the preferred embodiment in that device 10 measures magnetically induced voltages from syringe 32 rather than electric current I. To measure and record a dose, the patient first presses cap 38 of syringe 32 against placement field 16. Voltage difference V is applied by generator 26 across input contact 22 and output contact 24, which are contacting input terminal 42 and output terminal 44, respectively. Voltage difference V causes current I to flow through a conducting path comprising input terminal 42, strip 46, rim 52, terminal 72, inductor 74, terminal 76, line 78, and output terminal 44. This produces a changing magnetic field B inside inductor 74 and along its axis. In particular, changing magnetic field B passes through measuring loop 70.

The intensity of magnetic field B passing through loop 70 is described by a magnetic flux $\phi$. Flux $\phi$ is equal to the area of loop 70 times B. Changing magnetic field B results in changing flux $\phi$, which, in turn, induces a voltage $\epsilon$ in loop 70 according to the well-known equation $\epsilon=-d\phi/dt$.

Magnetically active core 82 changes the intensity of magnetic field B depending on the portion of core 82 that is inside inductor 74. Thus, as plunger 36 advances inside barrel 50 and a larger portion of core 82 is contained inside inductor 74, the rate of change of flux $d\phi/dt$ changes as well. Based on the above equation, this alters magnetically induced voltage $\epsilon$ in loop 70. Thus, a measurement of induced voltage $\epsilon$ produces electrical data indicating the position of plunger 36 inside barrel 50, and thus the size of dose 34 contained in barrel 50.

Induced voltage $\epsilon$ is measured by voltage meter 68 and recorded in memory 31. Once the measurement of induced voltage $\epsilon$ indicating the size of dose 34 has been recorded in memory 31, the operation and advantages of this embodiment are identical to the operation and advantages of the preferred embodiment described above.

Figure 7:
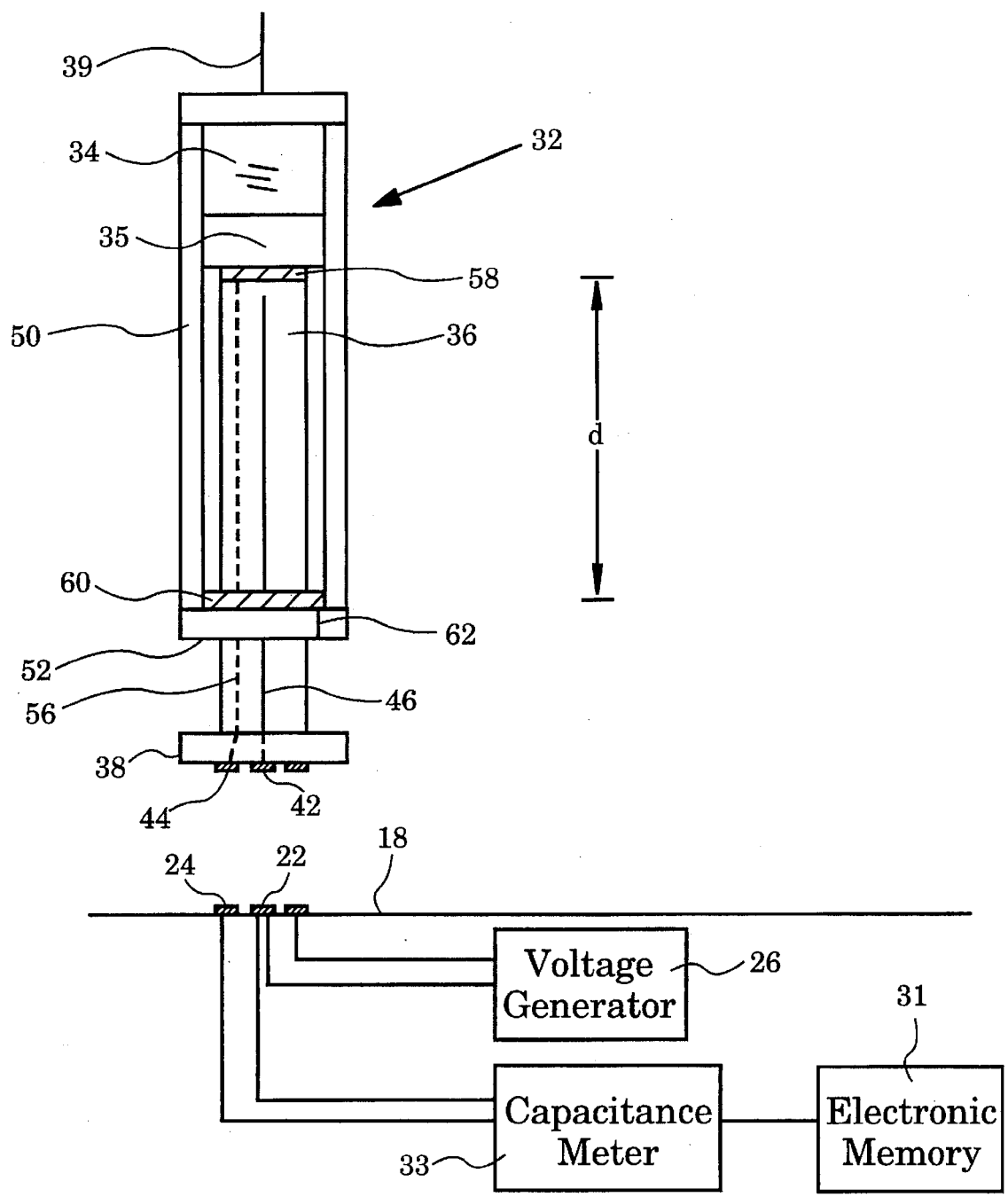
FIG. 7 is a schematic view and partial block diagram of another injection syringe being placed on another metering device for dose measurement.

A fifth embodiment of the invention, designed to measure a capacitance of syringe 32, is shown in FIG. 7. Ammeter 28 is eliminated and device 10 now has a capacitance meter 33 connected to input contact 22 and output contact 24. Capacitance meter 33 is connected to memory 31 such that memory 31 can record a capacitance measurement received from capacitance meter 33.

Referring to syringe 32, resistive strip 48 is replaced with a second conducting strip 56. Strip 56 is connected at one end to output terminal 44, then routed through cap 38 and inside plunger 36, to ensure that strip 56 does not contact rim 52. The other end of strip 56 is connected to a conducting plate 58 at the junction of plunger 36 with a piston section 35. Plate 58 covers the entire cross section of plunger 36 and is made of an electrically conductive material.

Conducting strip 46 is guided, as before, on the surface of plunger 36 and is in electrical contact with rim 52. A conducting ring 60 is located between barrel 50 and plunger 36. Ring 60 is immobile and in electrical contact with rim 52 through a junction 62. Furthermore, ring 60 has a sufficient surface area to act as a capacitive element in conjunction with conducting plate 58. While a slight capacitance exists between strip 46 and strip 56 it is negligible in comparison to the capacitance of ring 60 and plate 58.

The operation of the fifth embodiment is shown in FIG. 7. As described in the preferred embodiment, the patient first presses cap 38 of syringe 32 against placement field 16 so that input contact 22 contacts input terminal 42, and output contact 24 contacts output terminal 44. Meanwhile, voltage difference V is applied by generator 26 across input contact 22 and output contact 24.

Voltage difference V causes current I to flow to plate 58 and ring 60 and remain there in the form of accumulated charge. This condition is governed by the capacitance equation $V=Q/C$, where C is the capacitance of the system including plate 58 and ring 60. In turn, capacitance C is determined by the equation $C=A\epsilon_o/d$ where A is the surface area on which the charge accumulates, $\epsilon_o$ is a constant, and d is the distance between ring 60 and plate 58. Since the surface area A of ring 60 and plate 58 remain constant, capacitance C is just inversely proportional to distance d. Meanwhile, distance d defines the position of plunger 36 in barrel 50, so that a measurement of capacitance C indicates the length of plunger 36 inside barrel 50. As explained in the preferred embodiment above, the length of plunger 36 inside barrel 50 defines the size of dose 34 contained in barrel 50.

Thus, a measurement of capacitance C provides electrical data indicating the size of dose 34. Capacitance meter 33 measures capacitance C, and records this measurement in memory 31. Once the measurement of capacitance C has been recorded in memory 31, the operation and advantages of this embodiment are the same as the operation and advantages of the preferred embodiment described above.

Figure 8:
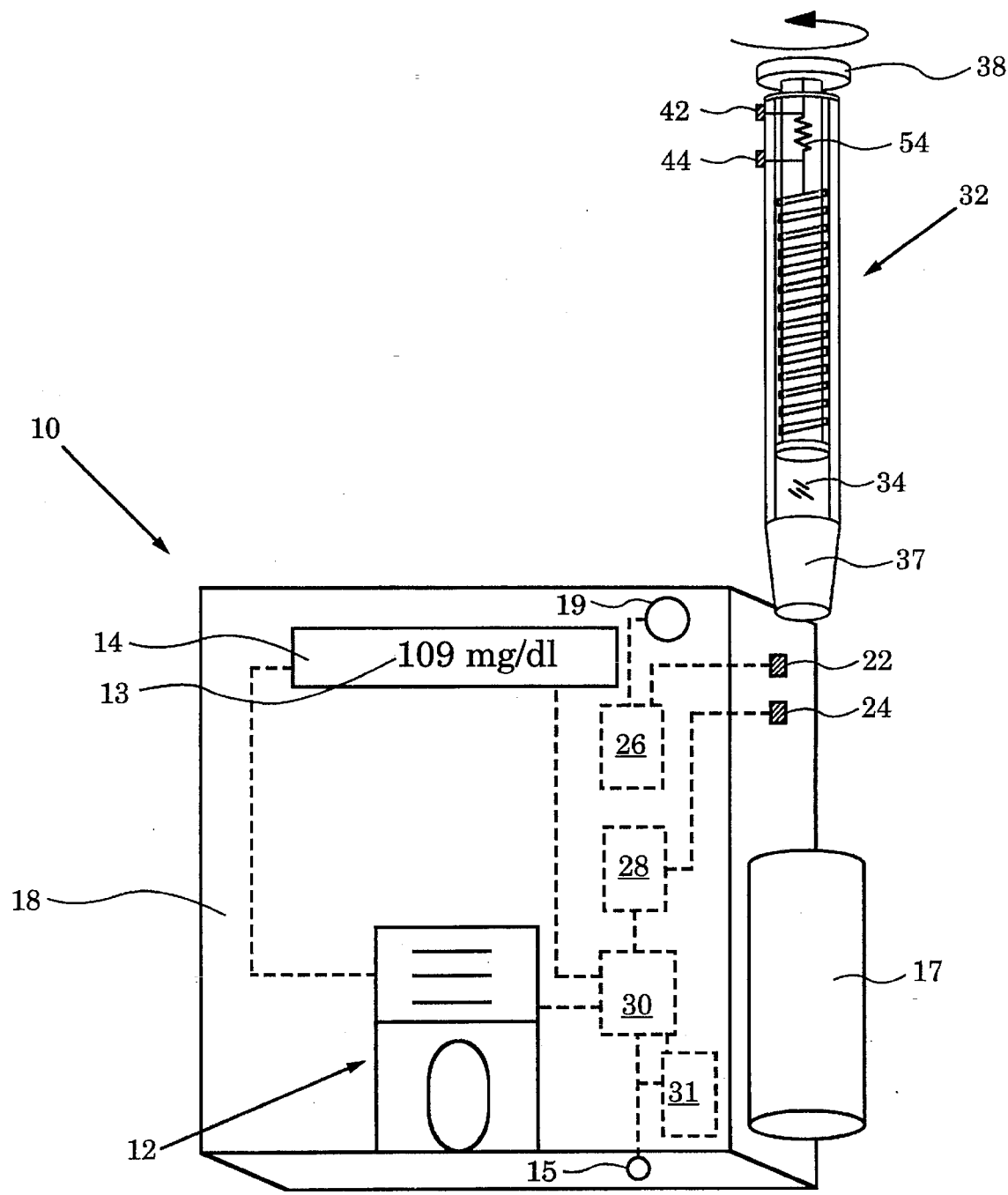
FIG. 8 is a schematic view of another injection syringe being placed into a holder of another metering device for dose measurement.

A sixth embodiment of the invention is shown in FIG. 8. In this embodiment, device 10 has a holder 17 for holding a pre-filled, rotatable plunger syringe 32. Placement field 16 is eliminated and input contact 22 and output contact 24 are now located on an outer side surface of housing 11. Voltage generator 26 is connected to apply a voltage V to input contact 22. However, now a button 19 is located on face plate 18. Button 19 is connected to voltage generator 26 such that voltage generator 26 only applies voltage V when button 19 is depressed.

Syringe 32 has a rotatable cap 38 enabling the user to preset dose 34 by rotating cap 38. Such syringes are disclosed in U.S. Pat. No. 5,104,380 and U.S. Pat. No. 5,226,895. Rotatable cap 38 is mechanically joined to a potentiometer 54 such that when cap 38 is rotated, potentiometer 54 is rotated by the same amount. Input terminal 42 and output terminal 44 are located on an outer side surface of barrel 50 and electrically connected to opposite sides of potentiometer 54. This creates a conducting path through syringe 32 comprising terminal 42, potentiometer 54, and terminal 44. Additionally, a safety shield 37 is placed over the end of syringe 32 having an injection needle (not shown).

Holder 17 is located on an outer side surface of housing 11, and is made of a non-electrically conductive material, preferably plastic. Holder 17 is a hollow cylinder having an open top and a flat bottom surface. Holder 17 has an inner diameter slightly larger than the diameter of syringe 32 such that syringe 32 can be inserted inside the hollow middle of holder 17. Further, the length of holder 17 is shorter than the length of syringe 32 such that cap 38, input terminal 42, and output terminal 44 of syringe 32 are not inside holder 17 when syringe 32 is fully inserted into holder 17. Holder 17, input contact 22, and output contact 24 are located on housing 11 such that input contact 22 and output contact 24 establish contact with input terminal 42 and output terminal 44 respectively when syringe 32 is fully inserted into holder 17.

The operation of the sixth embodiment is shown in FIG. 8. The patient places syringe 32 into holder 17 by inserting the end of syringe 32 having shield 37 into holder 17 until shield 37 contacts the bottom of holder 17. When syringe 32 is inserted into holder 17, input contact 22 and output contact 24 establish electrical contact with input terminal 42 and output terminal 44 respectively. Syringe 32 is stored in holder 17 in this manner until the patient desires to use syringe 32 to inject a medication.

To inject a medication, the patient first rotates cap 38 to preset a desired dose 34 to be injected. When cap 38 is rotated, potentiometer 54 is rotated by the same amount because of its mechanical connection with cap 38. The resistance of potentiometer 54 is changed proportionally to the amount of rotation. Next, the patient presses button 19 to activate voltage generator 26. Voltage generator 26 applies voltage V to input contact 22, which is contacting input terminal 42. Voltage V causes electric current I to flow through a conducting path comprising terminal 42, potentiometer 54, and terminal 44.

Based on Ohm's law, which states that I=V/R, current I is inversely proportional to the total resistance R of the conducting path. Because voltage V is constant, current I varies only with the total resistance R of the conducting path. Since all parts of the conducting path have negligible resistance in comparison to potentiometer 54, the total resistance R of the conducting path is the resistance set on potentiometer 54. Thus, current I is directly proportional to the amount that potentiometer 54 has been rotated. The amount that potentiometer 54 has been rotated is directly proportional to the size of dose 34 preset by the patient.

Thus, a measurement of current I produces electrical data corresponding to the size of dose 34. Ammeter 28 measures current I and records the measurement in memory 31. Once the measurement of current I has been recorded, the operation and advantages of this embodiment are the same as the operation and advantages of the preferred embodiment described above.

SUMMARY, RAMIFICATIONS, AND SCOPE

Although the above description includes many specifities, these should not be construed as limiting the scope of the invention, but merely as illustrating some of the presently preferred embodiments. Many other embodiments are possible. For example, placement field 16 can have other shapes than a circle delineated on face plate 18. Placement field 16 could be square, hexagonal, or any other shape that aids a patient in placing syringe 32 on device 10. Additionally, placement field 16 could be recessed in face plate 18 so that positioning studs 20 are not necessary.

In embodiments that include a holder 17 for syringe 32, the holder 17 could be located in positions other than a side surface of housing 11. A receptacle for receiving the syringe could be built into the housing 11 of device 10 so that the syringe could be stored inside housing 11.

Furthermore, device 10 is not limited to having just one meter 12 for measuring a patient's physical condition. Device 10 could have multiple meters for testing a patient. Also, device 10 need not be limited to measuring and recording doses from only one size syringe 32. Device 10 could have a user-programmable microprocessor that a patient programs to convert measurements from syringes of different sizes. Moreover, device 10 is not limited to aiding a self-care diabetes program. It could be incorporated into other medical devices to aid in the administration of any treatment plan that requires injections.

Therefore, the scope of the invention should be determined not by the examples given but by the appended claims and their legal equivalents.

I claim:

1. A device for electrically measuring and recording a dose contained in a syringe, said syringe having an input terminal, said device comprising:

a) an input contact for contacting said input terminal;

b) a holder for holding said syringe, said holder and said input contact being positioned such that when said syringe is inserted in said holder, said input contact contacts said input terminal;

c) a voltage generator connected to said input contact for applying a voltage to said input terminal when said input contact contacts said input terminal;

d) a measuring means for measuring an electrical response from said syringe, said electrical response resulting from said voltage and indicating a size of said dose; and e) an electronic recording means for recording the measurement of said electrical response.

2. The device of claim 1, further comprising a data port connected to said electronic recording means for transmitting recorded measurements from said electronic recording means to a host computer.

3. The device of claim 1, further comprising a testing means for testing a physical condition of a patient and for producing a digital value representative of said physical condition, said testing means being connected to said electronic recording means such that said electronic recording means records said digital value representative of said physical condition.

4. The device of claim 3, wherein said testing means comprises a blood glucose meter and said physical condition comprises a blood glucose level.

5. The device of claim 3, further comprising a display means connected to said testing means for displaying said digital value representative of said physical condition.

6. The device of claim 1, further comprising a converting means for converting the measurement of said electrical response into a digital value representative of said dose, said converting means being connected between said measuring means and said electronic recording means such that said electronic recording means records said digital value representative of said dose.

7. The device of claim 6, further comprising a display means connected to said converting means for displaying said digital value representative of said dose.

8. The device of claim 1, wherein said device is installed in a housing sufficiently compact to enable said device to be hand-held and carried by a patient.

9. The device of claim 1, wherein said syringe has an output terminal, said electrical response comprises an electric current flowing between said input terminal and said output terminal, and wherein said measuring means comprises:

a) an output contact for contacting said output terminal, said output contact being positioned such that when said syringe is placed in said holder, said output contact contacts said output terminal; and b) an ammeter connected to said output contact for measuring said electric current at said output terminal when said output contact contacts said output terminal.

10. A method for electrically measuring and recording a dose contained in a syringe, said syringe having an input terminal, said method comprising the following steps:
   a) providing a metering device having a holder for said syringe, an input contact for contacting said input terminal, and a voltage generator connected to said input contact;
   b) inserting said syringe into said holder such that said input contact contacts said input terminal;
   c) applying to said input terminal a voltage generated by said voltage generator;
   d) measuring an electrical response from said syringe, said electrical response resulting from said voltage and indicating a size of said dose; and
   e) recording the measurement of said electrical response in an electronic memory.

11. The method of claim 10, further comprising the step of transmitting recorded measurements from said electronic memory to a host computer.

12. The method of claim 10, further comprising the steps of converting the measurement of said electrical response into a digital value representative of said dose and recording said digital value in said electronic memory.

13. The method of claim 12, further comprising the step of displaying said digital value on a display.

14. The method of claim 12, further comprising the step of transmitting said digital value from said electronic memory to a host computer.

15. The method of claim 10, further comprising the steps of testing a physical condition of a patient, producing a digital value representative of said physical condition, and recording said digital value in said electronic memory.

16. The method of claim 15, further comprising the step of displaying said digital value on a display.

17. The method of claim 15, further comprising the step of transmitting said digital value from said electronic memory to a host computer.

* * * * *